United States Patent [19]
Livak et al.

[11] Patent Number: 5,538,848
[45] Date of Patent: Jul. 23, 1996

[54] METHOD FOR DETECTING NUCLEIC ACID AMPLIFICATION USING SELF-QUENCHING FLUORESCENCE PROBE

[75] Inventors: Kenneth J. Livak, San Jose; Susan J. A. Flood, Fremont; Jeffrey Marmaro, Foster City, all of Calif.

[73] Assignee: Applied Biosystems Division, Perkin-Elmer Corp., Foster City, Calif.

[21] Appl. No.: 340,558

[22] Filed: Nov. 16, 1994

[51] Int. Cl.$^6$ .............. C12Q 1/68; C12Q 1/70; C12P 19/34; C07H 21/04
[52] U.S. Cl. .............. 435/5; 435/5; 435/91.2; 536/24.3; 536/24.31; 536/24.33; 536/26.6
[58] Field of Search .............. 435/6, 91.2, 5; 536/24.3–.33, 26.6

[56] References Cited

U.S. PATENT DOCUMENTS

| | | | |
|---|---|---|---|
| 4,220,450 | 4/1978 | Maggio | 23/230 |
| 5,210,015 | 5/1993 | Gelfand | 435/6 |
| 5,332,659 | 7/1994 | Kidwell | 435/6 |

FOREIGN PATENT DOCUMENTS

| | | |
|---|---|---|
| 0229943A2 | 12/1986 | European Pat. Off. |
| 0601889A2 | 12/1993 | European Pat. Off. |
| WO90/03446 | 4/1990 | WIPO |
| WO92/02638 | 2/1992 | WIPO |

OTHER PUBLICATIONS

Mergny et al Fluorescent energy transfer as a probe for nucleic acid structures and sequences. NAR 22:920–928, 1994.

Heller et al, "Fluorescent energy transfer oligonucleotide probes", Abstract 248, Fed. Proc., 46: 1968 (1987).

Holland, et al, "Detection of specific polymerase chain reaction product by utilizing the 5'→3' exonuclease activity of *Thermus aquaticus* DNA polymerase", Proc. Natl. Acad. Sci., 88: 7276–7280 (1991).

Higuchi et al, "Kinetic PCR analysis: real—time monitoring of DNA amplication reactions", Biotechnology, 11: 1026–1030 (1993).

Higuchi et al, "Simultaneous amplification and detection of specific DNA sequences," Biotechnology, 10: 413–417 (1992).

Clegg, "Fluorescence resonance energy transfer and nucleic acids," Methods of Enzymology, 211: 353–389 (1992).

Wu et al, "Resonance energy transfer: methods and applications," Anal. Biochem. 218: 1–13 (1994).

Stryer et al, "Energy transfer: a spectroscopic ruler," Proc. Natl. Acad. Sci. 58: 719–726 (1967).

Clegg et al, "Observing the helical geometry of double-stranded DNA in solution by fluorescence resonance energy transfer," Proc. Natl. Acad. Sci., 90: 2994–2998 (1993).

Cardullo et al, "Detection of nucleic acid hybridization by nonradiative fluorescence resonance energy transfer," Proc. Natl. Acad. Sci., 85: 8790–8794 (1988).

Lee et al, "Allelic discrimination by nick–translation PCR with fluorogenic probes," Nucleic Acids Research, 21: 3761–3766 (1993).

Ozaki et al, "The estimation of distances between specific backbone–labeled sites in DNA using fluorescence resonance energy transfer," Nucleic Acids Research, 20: 5205–5214 (1992).

*Primary Examiner*—W. Gary Jones
*Assistant Examiner*—Dianne Rees
*Attorney, Agent, or Firm*—Haynes & Davis

[57] ABSTRACT

A method is provided for monitoring the progress of nucleic acid amplifications that rely on a nucleic acid polymerase having 5'→3' exonuclease activity. An important feature of the method is providing an oligonucleotide probe having a reporter molecule and a quencher molecule at either end such that the quencher molecule substantially quenches any fluorescence from the reporter whenever the oligonucleotide probe is in a single stranded state and such that the reporter is substantially unquenched whenever the oligonucleotide probe is in a double stranded state hybridized to a target polynucleotide.

24 Claims, 1 Drawing Sheet

METHOD FOR DETECTING NUCLEIC ACID AMPLIFICATION USING SELF-QUENCHING FLUORESCENCE PROBE

The invention relates generally to the field of nucleic acid amplification, and more particularly, to methods of monitoring the progress of nucleic acid amplification reactions, especially polymerase chain reactions (PCR).

BACKGROUND

Nucleic acid amplification techniques have opened broad new approaches to genetic testing and DNA analysis, e.g. Arnheim and Erlich, Ann. Rev. Biochem., 61: 131–156 (1992). PCR in particular has become a research tool of major importance with applications in cloning, analysis of genetic expression, DNA sequencing, genetic mapping, drug discovery, and the like, e.g. Arnheim et al (cited above); Gilliland et at, Proc. Natl. Acad. Sci., 87:2725–2729 (1990); Bevan et at, PCR Methods and Applications, 1:222–228 (1992); Green et at, PCR Methods and Applications, 1: 77–90 (1991); Blackwell et al, Science, 250:1104–1110 (1990). The widespread applications of such nucleic acid amplification techniques has driven the development of instrumentation for carrying out the amplification reactions under a variety of circumstances. Important design goals for such instrument development have included fine temperature control, minimization of sample-to-sample variability in multi-sample thermal cycling, automation of pre- and post-reaction processing steps, high speed temperature cycling, minimization of sample volumes, real time measurement of amplification products, minimization of cross-contamination, or "sample carryover," and the like. In particular, the design of instruments permitting amplification to be carried out in closed reaction chambers and monitored in real time would be highly desirable for preventing cross-contamination, e.g. Higuchi et al, Biotechnology, 10:413–417 (1992) and 11: 1026–1030(1993); and Holland et al, Proc. Natl. Acad. Sci., 88: 7276–7280 (1991). Clearly, the successful realization of such a design goal would be especially desirable in the analysis of diagnostic samples, where a high frequency of false positives and false negatives—caused by "sample carryover"—would severely reduce the value of an amplification procedure. Moreover, real time monitoring of an amplification reaction permits far more accurate quantitation of starting target DNA concentrations in multiple-target amplifications, as the relative values of close concentrations can be resolved by taking into account the history of the relative concentration values during the reaction. Real time monitoring also permits the efficiency of the amplification reaction to be evaluated, which can indicate whether reaction inhibitors are present in a sample.

Holland et al (cited above) and others have proposed fluorescence-based approaches to provide real time measurements of amplification products during a PCR. Such approaches have either employed intercalating dyes (such as ethidium bromide) to indicate the amount of double stranded DNA present, or they have employed probes containing fluorester-quencher pairs (the so-called "Tac-Man" approach) that are cleaved during amplification to release a fluorescent product whose concentration is proportional to the amount of double stranded DNA present.

The latter approach, illustrated in FIG. 1, involves the use of an oligonucleotide probe that specifically anneals to a region of the target polynucleotide "downstream," i.e. in the direction of extension, of primer binding sites. The probe contains a fluorescent "reporter" molecule and a "quencher" molecule such that the whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe anneals to the template where it is digested by the 5'→3' exonuclease activity of the polymerase. Upon digestion, the quencher molecule is no longer close enough to the reporter molecule to quench emissions by energy transfer. Thus, as more and more probe gets digested during amplification, a stronger and stronger fluorescent signal is generated.

Three main factors determine the performance of such a doubly labeled fluorescent probe: First is the degree of quenching observed in the intact unbound probe. This can be characterized by the ratio, designated herein as "$RQ^-$", of fluorescent emissions of the reporter molecule and the quencher molecule absent hybridization to a complementary polynucleotide. That is, $RQ^-$ is the ratio of fluorescent emissions of the reporter molecule and the quencher molecule when the S oligonucleotide probe is in a single stranded state. Influences on the value of $RQ^-$ include the particular reporter and quencher molecules used, the spacing between the reporter and quencher molecules, nucleotide sequence-specific effects, the degree of flexibility of structures, e.g. linkers, to which the reporter and quencher molecules are attached, the presence of impurities, and the like, e.g. Wu et at, Anal. Biochem., 218: 1–13 (1994); and Clegg, Meth. Enzymol., 211:353–388 (1992). (A related quantity, $RQ^+$, is the ratio of fluorescent emissions of the reporter molecule and the quencher molecule when the oligonucleotide probe is in a double stranded state with a complementary polynucleotide). A second factor is the efficiency of hybridization, which depends on probe melting temperature, $T_m$, the presence of secondary structure in the probe or target polynucleotide, annealing temperature, and other reaction conditions. Finally, a third factor is the efficiency at which the DNA polymerase 5'→3' exonuclease activity cleaves the bound probe between the reporter molecule and quencher molecule. Such efficiency depends on the proximity of the reporter or quencher to the 5' end of the probe, the "bulkiness" of the reporter or quencher, the degree of complementarity between the probe and target polynucleotide, and like factors, e.g. Lee et al, Nucleic Acids Research, 21:3761–3766 (1993).

As quenching is completely dependent on the physical proximity of the reporter molecule and quencher molecule, it has been assumed that the quencher and reporter molecules must be attached to the probe within a few nucleotides of one another, usually with a separation of about 6–16 nucleotides, e.g. Lee et al (cited above); Mergny et at, Nucleic Acids Research, 22:920–928 (1994); Cardullo et at, Proc. Natl. Acad. Sci., 85:8790–8794 (1988); Clegg et at, Proc. Natl. Acad. Sci., 90:2994–2998 (1993); Ozaki et at, Nucleic Acids Research, 20:5205–5214 (1992); and the like. Typically, this separation is achieved by attaching one member of a reporter-quencher pair to the 5' end of the probe and the other member to a base 6–16 nucleotides away. Unfortunately, there are at least two significant drawbacks to this arrangement. First, attaching reporter or quencher molecules typically involves more difficult chemistry than, for example, that used to attach moieties to an end. And second, attachment of reporter or quencher molecules to internal nucleotides adversely affects hybridization efficiency, e.g. Ward et at, U.S. Pat. No. 5,328,824; Ozaki et al (cited above); and the like.

In view of the above, the application of techniques for real-time monitoring of nucleic acid amplification would be

SUMMARY OF THE INVENTION

A broad object of our invention is to provide a method for real-time quantitation of nucleic amplification that employs a probe which is easier to synthesize than currently used probes and which has superior hybridization efficiency than those of currently used probes.

Another object of our invention is to provide a probe for use in the above method that has different fluorescent characteristics depending on whether it is in a double stranded state hybridized to a complementary polynucleotide or whether it is in a single stranded state.

Still another object of our invention is to provide a conveniently synthesized probe for use in the above method that has a reporter molecule attached to one end and a quencher molecule attached to the other end.

Another object of our invention is to provide a probe for use in the above method that does not require reporter or quencher moieties to be attached to internal bases or internucleotide linkages.

These and other objects of the invention are achieved in the method described below.

Generally the method of our invention relates to monitoring the progress of a nucleic acid amplification reaction that employs a nucleic acid polymerase having 5'→3' exonuclease activity. More particularly, our invention relates to a method of monitoring the amplification of a target polynucleotide by (1) providing an oligonucleotide probe capable of annealing to the target polynucleotide, the oligonucleotide probe having a reporter molecule capable of fluorescing attached to a first end and a quencher molecule attached to a second end such that the quencher molecule substantially quenches any fluorescence of the reporter molecule whenever the oligonucleotide probe is in a single-stranded state and such that the reporter is substantially unquenched whenever the oligonucleotide probe is in a double-stranded state; and (2) extending a primer annealed to the target polynucleotide with a nucleic acid polymerase having 5'→3' exonuclease activity such that the oligonucleotide probe is degraded by the 5'→3' exonuclease activity of the nucleic acid polymerase as it extends the primer.

Preferably, reporter and quencher molecules are attached to the terminal 5' carbon and terminal 3' carbon of the oligonucleotide probe by way of 5' and 3' linking moieties, respectively, such that either the reporter molecule is on the 5' end of the probe and the quencher molecule is on the 3' end of the probe, or the reporter molecule is on the 3' end of the probe and the quencher molecule is on the 5' end of the probe.

Our invention advantageously overcomes several deficiencies of currently used probes for monitoring the amplification of nucleic acids. In particular, probes provided in the method of our invention are readily synthesized and ameliorate inefficiencies in hybridization and exonuclease cleavage due to groups which are attached to internal bases or internucleotide linkages.

An important aspect of the invention is the discovery that in probe a quencher molecule need not be attached to a nucleotide adjacent to a reporter molecule to successfully quench fluorescence produced by the reporter when the probe is in a single stranded state. Thus, facilely synthesized end-labeled probes may be used in place of more-difficult-to-synthesize and less efficient internally labeled probes for monitoring nucleic acid amplification.

DETAILED DESCRIPTION OF THE INVENTION

Figure 1:
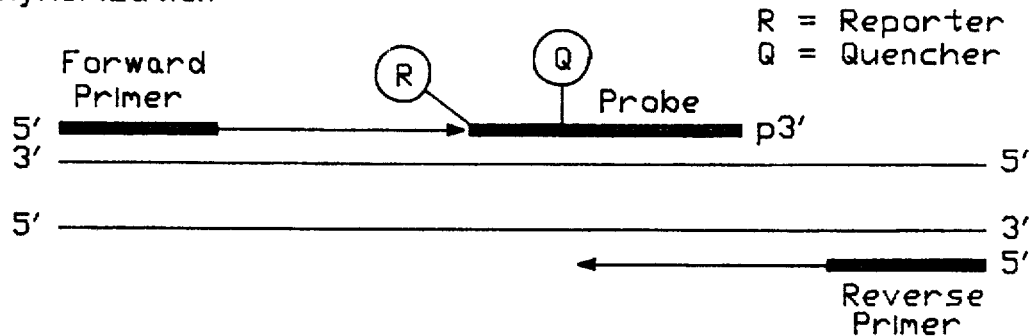
FIG. 1 illustrates a method for real-time monitoring nucleic acid amplification utilizing a probe which is degraded by the 5'→3' exonuclease activity of a nucleic acid polymerase.
Figure 1:
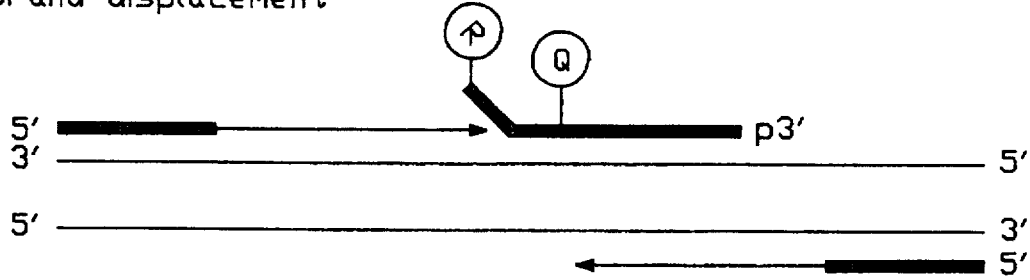
Figure 1:
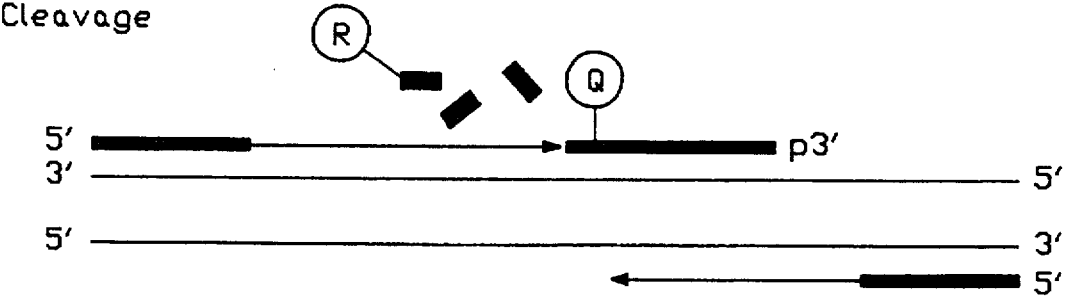
Figure 1:
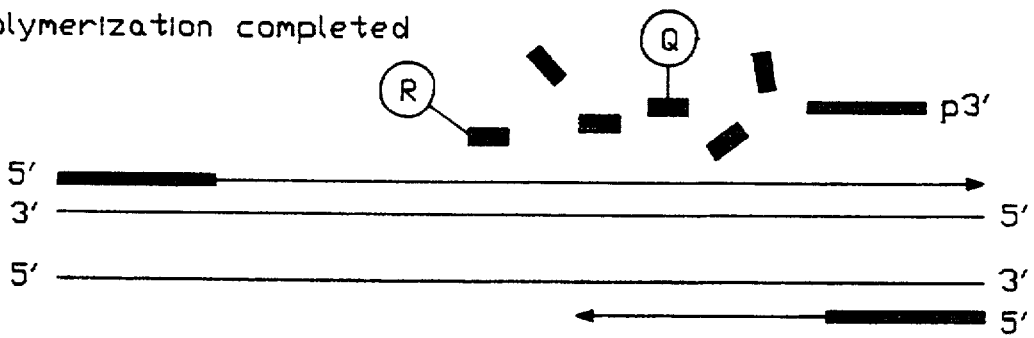

Preferably, the method of the invention is used in conjunction with the amplification of a target polynucleotide by PCR, e.g. as described in many references, such as Innis et at, editors, PCR Protocols (Academic Press, New York, 1989); Sambrook et at, Molecular Cloning, Second Edition (Cold Spring Harbor Laboratory, New York, 1989); and the like. The binding site of the oligonucleotide probe is located between the PCR primers used to amplify the target polynucleotide. Preferably, PCR is carried out using Taq DNA polymerase, e.g. Amplitaq™ (Perkin-Elmer, Norwalk, Conn.), or an equivalent thermostable DNA polymerase, and the annealing temperature of the PCR is about 5°–10° C. below the melting temperature of the oligonucleotide probes employed.

The term "oligonucleotide" as used herein includes linear oligomers of natural or modified monomers or linkages, including deoxyribonucleosides, ribonucleosides, and the like, capable of specifically binding to a target polynucleotide by way of a regular pattern of monomer-to-monomer interactions, such as Watson-Crick type of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. Generally, oligonucleotide probes of the invention will have a sufficient number of phosphodiester linkages adjacent to its 5' end so that the 5'→3' exonuclease activity employed can efficiently degrade the bound probe to separate the reporter and quencher molecules.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. Conversely, a "mismatch" in a duplex between a target polynucleotide and an oligonucleotide probe or primer means that a pair of nucleotides in the duplex fails to undergo Watson-Crick bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90:543–584 (1990), or the like, with the only proviso that they are capable of specific hybridization. Such analogs include synthetic nucleosides designed to enhance binding properties, reduce degeneracy, increase specificity, and the like.

Oligonucleotide probes of the invention can be synthesized by a number of approaches, e.g. Ozaki et at, Nucleic Acids Research, 20:5205–5214 (1992); Agrawal et at, Nucleic Acids Research, 18:5419–5423 ( 1990); or the like. The oligonucleotide probes of the invention are conveniently synthesized on an automated DNA synthesizer, e.g. an Applied Biosystems, Inc. Foster City, Calif.) model 392 or 394 DNA/RNA Synthesizer, using standard chemistries, such as phosphoramidite chemistry, e.g. disclosed in the following references: Beaucage and Iyer, Tetrahedron, 48:2223–2311 (1992); Molko et al, U.S. Pat. Nos. 4,980, 460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected. Preferably, the oligonucleotide probe is in the range of 15–60 nucleotides in length. More preferably, the oligonucleotide probe is in the range of 18–30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the above-cited references describing the "tatman" type of assays.

Preferably, the 3' terminal nucleotide of the oligonucleotide probe is blocked or rendered incapable of extension by a nucleic acid polymerase. Such blocking is conveniently carried out by the attachment of a reporter or quencher molecule to the terminal 3' carbon of the oligonucleotide probe by a linking moiety.

Preferably, reporter molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to herein as chromogenic molecules.

There is a great deal of practical guidance available in the literature for selecting appropriate reporter-quencher pairs for particular probes, as exemplified by the following references: Clegg (cited above); Wu et al (cited above); Pesce et at, editors, Fluorescence Spectroscopy (Marcel Dekker, New York, 1971); White et at, Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g. Berlman, Handbook of Fluorescence Sprectra of Aromatic Molecules, 2nd Edition (Academic Press, New York, 1971 ); Griffiths, Colour and Consitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al, U.S. Pat. No. 3,996,345; Khanna et al, U.S. Pat. No. 4,351,760; and the like.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, reporter and quencher molecules are selected from fluorescein and rhodamine dyes. These dyes and appropriate linking methodologies for attachment to oligonucleotides are described in many references, e.g. Khanna et al (cited above); Marshall, Histochemical J., 7:299–303 (1975); Mechnen et at, U.S. Pat. No. 5,188,934; Menchen et al, European pat. No. application 87310256.0; and Bergot et al, International application PCT/US90/05565. The latter four documents are hereby incorporated by reference.

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991 ); Zuckerman et al, Nucleic Acids Research, 15: 5305–5321 (1987)(3' thiol group on oligonucleotide); Sharma et al, Nucleic Acids Research, 19:3019 (1991 )(3' sulfhydryl); Giusti et al, PCR Methods and Applications, 2:223–227 (1993) and Fung et al, U.S. Pat. No. 4,757,141 (5' phosphoamino group via Aminolink™ II available from Applied Biosystems, Foster City, Calif.); Stabinsky, U.S. Pat. No. 4,739,044 (3' aminoalkylphosphoryl group); Agrawal et al, Tetrahedron Letters, 31:1543–1546 (1990)(attachment via phosphoramidate linkages); Sproat et al, Nucleic Acids Research, 15:4837 (1987)(5' mercapto group); Nelson et al, Nucleic Acids Research, 17:7187–7194 (1989)(3' amino group); and the like.

Preferably, commercially available linking moieties are employed that can be attached to an oligonucleotide during synthesis, e.g. available from Clontech Laboratories (Palo Alto, Calif.).

Rhodamine and fluorescein dyes are also conveniently attached to the 5' hydroxyl of an oligonucleotide at the conclusion of solid phase synthesis by way of dyes derivatized with a phosphoramidite moiety, e.g. Woo et al, U.S. Pat. No. 5,231,191; and Hobbs, Jr. U.S. Pat. No. 4,997,928.

EXAMPLE

The method of the invention was carried out using the oligonucleotides shown in Table 1. Linker arm nucleotide ("LAN") phosphoramidite was obtained from Glen Research. Standard DNA phosphoramidites, 6-carboxyfluorescein ("6-FAM") phosphoramidite, 6-carboxytetramethylrhodamine succinimidyl ester ("TAMRA NHS ester"), and Phosphalink™ for attaching a 3' blocking phosphate were obtained from Perkin-Elmer, Applied Biosystems Division. Oligonucleotide synthesis was performed on a model 394 DNA Synthesizer (Applied Biosystems). Primer and complement oligonucleotides were purified using Oligo Purification Cartridges (Applied Biosystems). Doubly labeled probes were synthesized with 6-FAM-labeled phosphoramidite at the 5' end, LAN replacing one of the T's in the oligonucleotide sequence, and Phosphalink™ at the 3' end. Following deprotection and ethanol precipitation, TAMRA NHS ester was coupled to the LAN-containing oligonucleotide in 250 mM Na-bicarbonate buffer (pH 9.0) at room temperature. Unreacted dye was removed by passage over a PD-10 Sephadex column. Finally, the doubly labeled probe was purified by preparative HPLC using standard protocols. Below, probes are named by designating the sequence from Table 1 and the position of the LAN-TAMRA moiety. For example, probe A1-7 has sequence of A1 with LAN-TAMRA at nucleoside position 7 from the 5' end.

All PCR amplifications were performed in a Perkin-Elmer Thermocycler 9600 using 50 µl reactions that contained 10 mM Tris-HCl (pH 8.3), 50 mM KCl, 200 µM dATP, 200 µM dCTP, 200 µM dGTP, 400 µM dUTP, 0.5 units AmpErase™ uracil N-glycolyase (Perkin-Elmer), and 1.25 units AmpliTaq™ (Perkin-Elmer). A 295 basepair segment of exon 3 of the β-human 13-actin gene (nucleotides 2141–2435 disclosed by Nakajima-Iijima) was amplified using the AFP and ARP primers listed below. The amplification reactions contained 4 µM MgCl$_2$, 20 ng human genomic DNA, 50 nM A1 or A3 probe, and 300 nM of each primer. Thermal regimen was 50° C. (2 min); 95° C. (10 min); 40 cycles of 95° C. (20 sec.), 60° C. (1 min); and hold at 72° C. A 515 basepair segment was amplified from a plasmid that consists of a segment of λ DNA (nucleotides 32,220–32,747) inserted into the Sma I site of vector pUC 119. These reactions contained 3.5 mM MgCl$_2$, 1 ng plasmid DNA, 50 nM P2 or P5 probe, 200 nM primer F119, and 200 nM primer R119. The thermal regimen was 50° C. (2 min); 95° C. (10 min); 25 cycles of 95° C. (20 sec.), 57° C. (1 min); and hold at 72° C.

For each amplification reaction, 40 µl was transferred to an individual well of a white 96-well microtiter plate (Perkin-Elmer). Fluorescence was measured on a Perkin-Elmer TaqMan™ LS-50B System, which consists of a luminescence spectrometer with a plate reader assembly, a 485 nm excitation filter, and a 515 nm emission filter. Excitation was carried out at 488 nm using a 5 nm slit width. Emission was measured at 518 nm for 6-FAM (the reporter, or R value) and 582 nm for TAMRA (the quencher, or Q value) using a 10 nm slit width. In order to determine the increase in reporter emission that is due to cleavage of the probe during PCR, three normalizations are applied to the raw emission data. First, emission intensity of a buffer blank is subtracted for each wavelength. Second, emission intensity of the reporter is divided by the emission intensity of the quencher to give an RQ ratio for each reaction tube. This normalizes for well-to-well variation in probe concentration and fluorescence measurement. Finally, ΔRQ is calculated by subtracting the RQ value of the no template control (RQ$^-$) from the RQ value for the complete reaction including a template (RQ$^+$).

Three pairs of probes were tested in PCR assays. For each pair, one probe has TAMRA attached to an internal nucleotide and the other has TAMRA attached to the 3' end nucleotide. Results are shown in Table 2. For all three sets, the probe with the 3' quencher exhibits a ΔRQ value that is considerably higher than for the probe with the internal quencher.

Table 3 gives the results of fluorescence measurements of the indicated probes in single and double stranded states. For probes having reporter and quencher at opposite ends of the oligonucleotide, hybridization caused a dramatic increase in RQ.

TABLE 1

Sequences of oligonucleotides.

| Name | Type | Sequence |
|---|---|---|
| F119 | SEQ ID NO: 1 | primer | ACCCACAGGAACTGATCACCACTC |
| R119 | SEQ ID NO: 2 | primer | ATGTCGCGTTCCGGCTGACGTTCTGC |
| P2 | SEQ ID NO: 3 | probe | TCGCATTACTGATCGTTGCCAACCAGTp |
| P2C | SEQ ID NO: 4 | complement | GTACTGGTTGGCAACGATCAGTAATGCGATG |
| P5 | SEQ ID NO: 5 | probe | CGGATTTGCTGGTATCTATGACAAGGATp |
| P5C | SEQ ID NO: 6 | complement | TTCATCCTTGTCATAGATACCAGCAAATCCG |
| AFP | SEQ ID NO: 7 | primer | TCACCCACACTGTGCCCATCTACGA |
| ARP | SEQ ID NO: 8 | primer | CAGCGGAACCGCTCATTGCCAATGG |
| A1 | SEQ ID NO: 9 | probe | ATGCCCTCCCCCATGCCATCCTGCGTp |
| A1C | SEQ ID NO: 10 | complement | AGACGCAGGATGGCATGGGGGAGGGCATAC |
| A3 | SEQ ID NO: 11 | probe | CGCCCTGGACTTCGAAGCAAGAGATp |
| A3C | SEQ ID NO: 12 | complement | CCATCTCTTGCTCGAAGTCCAGGGCGAC |

TABLE 2

| | 518 | | 582 | | | | |
|---|---|---|---|---|---|---|---|
| Probe | no temp. | +temp. | no temp. | +temp. | RQ$^-$ | RQ$^+$ | ΔRQ |
| A3-6 | 34.06 | 50.12 | 73.78 | 70.83 | 0.46 | 0.71 | 0.25 |
| A3-24 | 58.85 | 202.27 | 69.66 | 78.81 | 0.84 | 2.57 | 1.72 |
| P2-7 | 67.58 | 341.15 | 85.78 | 87.87 | 0.79 | 3.89 | 3.10 |

TABLE 2-continued

| | 518 | | 582 | | | | |
|---|---|---|---|---|---|---|---|
| Probe | no temp. | +temp. | no temp. | +temp. | RQ⁻ | RQ⁺ | ΔRQ |
| P2-27 | 124.57 | 722.22 | 152.58 | 118.42 | 0.82 | 6.10 | 5.28 |
| P5-10 | 77.32 | 156.10 | 75.41 | 67.01 | 1.02 | 2.33 | 1.30 |
| P5-28 | 73.23 | 507.28 | 106.64 | 96.28 | 0.69 | 5.28 | 4.59 |

TABLE 3

| | 518 | | 582 | | RQ | |
|---|---|---|---|---|---|---|
| Probe | ss | ds | ss | ds | ss | ds |
| P2-7 | 63.81 | 84.07 | 96.52 | 142.97 | 0.66 | 0.59 |
| P2-27 | 92.31 | 557.53 | 165.13 | 89.47 | 0.56 | 6.23 |
| P5-10 | 266.30 | 366.37 | 437.97 | 491.00 | 0.61 | 0.75 |
| P5-28 | 51.91 | 782.80 | 141.20 | 154.07 | 0.37 | 5.08 |
| A1-7 | 18.40 | 60.45 | 105.53 | 218.83 | 0.17 | 0.28 |
| A1-26 | 87.75 | 734.37 | 90.91 | 118.57 | 0.97 | 6.19 |
| A3-6 | 44.77 | 104.80 | 90.80 | 177.87 | 0.49 | 0.59 |
| A3-24 | 45.57 | 857.57 | 100.15 | 191.43 | 0.46 | 3.47 |

We claim:

1. A method for monitoring nucleic acid amplification comprising:

performing nucleic acid amplification on a target polynucleotide using a nucleic acid polymerase having 5'–3' nuclease activity, a primer capable of hybridizing to said target polynucleotide, and an oligonucleotide probe capable of hybridizing to said target polynucleotide, 3' relative to said primer, said oligonucleotide probe having a fluorescent reporter molecule and a quencher molecule capable of quenching the fluorescence of said reporter molecule, said oligonucleotide probe existing in at least one single-stranded conformation when unhybridized where said quencher molecule quenches the fluorescence of said reporter molecule, said oligonucleotide probe existing in at least one conformation when hybridized to said target polynucleotide where the fluorescence of said reporter molecule is unquenched, the fluorescence intensity of said reporter molecule being greater than the fluorescence intensity of said quencher molecule when said probe is hybridized to said target; polynucleotide, said nucleic acid polymerase digesting said oligonucleotide probe during amplification to separate said reporter molecule from said quencher molecule; and monitoring the fluorescence of said reporter molecule, the generation of fluorescence corresponding to the occurrence of nucleic acid amplification.

2. The method according to claim 1 wherein said nucleic acid polymerase is a thermostable nucleic acid polymerase.

3. The method according to claim 1 wherein said reporter molecule is a fluorescein dye and said quencher molecule is a rhodemine dye.

4. The method according to claim 1 wherein said reporter molecule is separated from said quencher molecule by at least about 15 nucleotides.

5. The method according to claim 3 wherein said reporter molecule is separated from said quencher molecule by between about 15 and 60 nucleotides.

6. The method according to claim 1 wherein raid reporter molecule is separated from said quencher molecule by at least about 18 nucleotide.

7. The method according to claim 3 wherein said reporter molecule is separated from said quencher molecule by between about 18 and 30 nucleotides.

8. The method according to claim 1 wherein the reporter molecule is attached to a 3' terminal nucleotide of the probe.

9. The method according to claim 8 wherein the quencher molecule is attached to a 5' terminal nucleotide of the probe.

10. The method according to claim 1 wherein the reporter molecule is attached to a 5' terminal nucleotide of the probe.

11. The method according to claim 10 wherein the quencher molecule is attached to a 3' terminal nucleotide of the probe.

12. The method according to claim 1 wherein the quencher molecule is attached to a 3' terminal nucleotide of the probe.

13. The method according to claim 1 wherein the quencher molecule is attached to 5' terminal nucleotide of the probe.

14. A method for monitoring nucleic acid amplification comprising:

performing nucleic acid amplification on a target polynucleotide using a nucleic acid polymerase having 5'–3' nuclease activity, a primer capable of hybridizing to said target polynucleotide, and an oligonucleotide probe capable of hybridizing to said target polynucleotide 3' relative to said primer, said oligonucleotide probe having a fluorescent reporter molecule and a quencher molecule capable of quenching the fluorescence of said reporter molecule, said oligonucleotide probe existing in at least one single-stranded conformation when unhybridized where said quencher molecule quenches the fluorescence of said reporter molecule, said oligonucleotide probe existing in at least one conformation when hybridized to said target polynucleotide where the fluorescence of said reporter molecule is unquenched the fluorescence intensity of said oligonucleotide probe hybridized to said target polynucleotide being at least about a factor of 6 greater than the fluorescence intensity of said oligonucleotide probe when not hybridized to said target polynucleotide, said nucleic acid polymerase digesting said oligonucleotide probe during amplification to separate said reporter molecule from said quencher molecule; and monitoring the fluorescence of said reporter molecule, the generation of fluorescence corresponding to the occurrence of nucleic acid amplification.

15. The method according to claim 14 wherein said reporter molecule is separated from said quencher molecule by at least about 15 nucleotides.

16. The method according to claim 15 wherein said reporter molecule is separated from said quencher molecule by between about 15 and 60 nucleotides.

17. The: method according to claim 14 wherein the reporter molecule is attached to a 3' terminal nucleotide of the probe.

18. The method according to claim 17 wherein the quencher molecule is attached to a 5' terminal nucleotide of the probe.

19. The method according to claim 14 wherein the reporter molecule is attached to a 5' Terminal nucleotide of the probe.

20. The method according to claim 19 wherein the quencher molecule is attached to a 3' terminal nucleotide of the probe.

21. The method according to claim 14 wherein the quencher molecule is attached to a 5' terminal nucleotide of the probe.

22. The method according to claim 14 wherein the quencher molecule is attached to a 3' terminal nucleotide of the probe.

23. The method according to claim 1 wherein the fluorescence intensity of said reporter molecule is at least about a favor 3.5 greater than the fluorescence intensity of said quencher molecule when said probe is hybridized to said target polynucleotide.

24. A method for monitoring nucleic acid amplification comprising:

performing nucleic acid amplification on a target polynucleotide using a nucleic acid polymerase having 5'–3' nuclease activity, a primer capable of hybridizing to said target polynucleotide and an oligonucleotide probe capable of hybridizing to said target polynucleotide 3' relative to said primer, said oligonucleotide probe having a fluorescent reporter molecule and a quencher molecule capable of quenching the fluorescence of said reporter molecule, said oligonucleotide probe existing in at least one single-stranded conformation when unhybridized where said quencher molecule quenches the fluorescence of said reporter molecule, said oligonucleotide probe existing in at least one conformation when hybridized to said target polynucleotide where the fluorescence of said reporter molecule is unquenched, the ratio of the fluorescence intensities of said reporter molecule to said quencher molecule when said probe is hybridized to said target polynucleotide being at least about a factor of 6 greater than the ratio of the fluorescence intensities of said reporter molecule to said quencher molecule when said probe is single-stranded, said nucleic acid polymerase digesting said oligonucleotide probe during amplification to separate said reporter molecule from said quencher molecule; and monitoring the fluorescence of said reporter molecule, the generation of fluorescence corresponding to the occurrence of nucleic acid amplification.

* * * * *

UNITED STATES PATENT AND TRADEMARK OFFICE
CERTIFICATE OF CORRECTION

PATENT NO.: 5,538,848

DATED: July 23, 1996

INVENTOR(S): Kenneth J. Livak, Susan J.A. Flood, and Jeffrey Marmaro

It is certified that error appears in the above-indentified patent and that said Letters Patent is hereby corrected as shown below:

Column 15, line 17, delete ":".

Column 16, line 1, delete "favor", insert --factor of--.

Signed and Sealed this

Fifth Day of August, 1997

Attest:

BRUCE LEHMAN

*Attesting Officer*  *Commissioner of Patents and Trademarks*

(12) EX PARTE REEXAMINATION CERTIFICATE (9336th)
United States Patent
Livak et al.

(10) Number: US 5,538,848 C1
(45) Certificate Issued: Oct. 5, 2012

(54) METHOD FOR DETECTING NUCLEIC ACID AMPLIFICATION USING SELF-QUENCHING FLUORESCENCE PROBE

(75) Inventors: Kenneth J. Livak, San Jose, CA (US); Susan J. A. Flood, Fremont, CA (US); Jeffrey Marmaro, Foster City, CA (US)

(73) Assignee: Applied Biosystems, LLC, Carlsbad, CA (US)

Reexamination Request:
No. 90/012,228, May 10, 2012

Reexamination Certificate for:
Patent No.: 5,538,848
Issued: Jul. 23, 1996
Appl. No.: 08/340,558
Filed: Nov. 16, 1994

Certificate of Correction issued Aug. 5, 1997.

(51) Int. Cl.
*C12N 15/09* (2006.01)
*C12N 15/00* (2006.01)
*C12Q 1/68* (2006.01)

(52) U.S. Cl. ......... 435/6.16; 435/5; 435/91.2; 536/24.3; 536/24.31; 536/24.33; 536/26.6

(58) Field of Classification Search .................. None
See application file for complete search history.

(56) References Cited

To view the complete listing of prior art documents cited during the proceeding for Reexamination Control Number 90/012,228, please refer to the USPTO's public Patent Application Information Retrieval (PAIR) system under the Display References tab.

*Primary Examiner* — Bruce Campell

(57) ABSTRACT

A method is provided for monitoring the progress of nucleic acid amplifications that rely on a nucleic acid polymerase having 5'→3' exonuclease activity. An important feature of the method is providing an oligonucleotide probe having a reporter molecule and a quencher molecule at either end such that the quencher molecule substantially quenches any fluorescence from the reporter whenever the oligonucleotide probe is in a single stranded state and such that the reporter is substantially unquenched whenever the oligonucleotide probe is in a double stranded state hybridized to a target polynucleotide.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-24 is confirmed.

* * * * *

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

ACCCACAGGA ACTGATCACC ACTC                      24

( 2 ) INFORMATION FOR SEQ ID NO: 2:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

ATGTCGCGTT CCGGCTGACG TTCTGC                    26

( 2 ) INFORMATION FOR SEQ ID NO: 3:

( i ) SEQUENCE CHARACTERISTICS:
        ( A ) LENGTH: 27 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 3:

TCGCATTACT GATCGTTGCC AACCA GT                27

( 2 ) INFORMATION FOR SEQ ID NO: 4:

( i ) SEQUENCE CHARACTERISTICS:
        ( A ) LENGTH: 31 nucleotides
        ( B ) TYPE: nucleic acid
        ( C ) STRANDEDNESS: single ( D ) TOPOLOGY: linear ( x i ) SEQUENCE DESCRIPTION: SEQ ID NO: 4:

GTACTGGTTG GCAACGATCA GTAATGCGAT G     31

( 2 ) INFORMATION FOR SEQ ID NO: 5:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 5:

CGGATTTGCT GGTATCTATG ACAAG GAT     28

( 2 ) INFORMATION FOR SEQ ID NO: 6:

( i ) SEQUENCE CHARACTERISTICS:
        ( A ) LENGTH: 31 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 6:

TTCATCCTTG TCATAGATAC CAGCAAATCC G     31

( 2 ) INFORMATION FOR SEQ ID NO: 7:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 7:

TCACCCACAC TGTGCCCATC TACGA     25

( 2 ) INFORMATION FOR SEQ ID NO: 8:

( i ) SEQUENCE CHARACTERISTICS:
        ( A ) LENGTH: 25 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CAGCGGAACC GCTCATTGCC AATGG     25

( 2 ) INFORMATION FOR SEQ ID NO: 9:

( i ) SEQUENCE CHARACTERISTICS:
        ( A ) LENGTH: 26 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 9:

ATGCCCTCCC CCATGCCATC CTGCGT     26

( 2 ) INFORMATION FOR SEQ ID NO: 10:

( i ) SEQUENCE CHARACTERISTICS:
        ( A ) LENGTH: 30 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 10:

AGACGCAGGA TGGCATGGGG GAGGGCATAC                30

( 2 ) INFORMATION FOR SEQ ID NO: 11:

( i ) SEQUENCE CHARACTERISTICS:
        ( A ) LENGTH: 24 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CGCCCTGGAC TTCGAGCAAG AGAT                      24

( 2 ) INFORMATION FOR SEQ ID NO: 12:

( i ) SEQUENCE CHARACTERISTICS:
        ( A ) LENGTH: 28 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 12:

CCATCTCTTG CTCGAAGTCC AGGGCGAC                  28